(12) United States Patent
Descour et al.

(10) Patent No.: US 7,864,380 B2
(45) Date of Patent: Jan. 4, 2011

(54) SLIDE-BORNE IMAGING INSTRUCTIONS

(75) Inventors: Michael R. Descour, Tucson, AZ (US);
Artur G. Olszak, Tucson, AZ (US);
Andrew Lowe, Chandler, AZ (US)

(73) Assignee: DMetrix, Inc., Tucson, AZ (US)

( * ) Notice: Subject to any disclaimer, the term of this patent is extended or adjusted under 35 U.S.C. 154(b) by 964 days.

(21) Appl. No.: 11/711,283

(22) Filed: Feb. 27, 2007

(65) Prior Publication Data
US 2007/0159688 A1 Jul. 12, 2007

Related U.S. Application Data

(63) Continuation-in-part of application No. 10/637,486, filed on Aug. 11, 2003, now Pat. No. 7,184,610, which is a continuation of application No. PCT/US02/08286, filed on Mar. 19, 2002.

(60) Provisional application No. 60/786,242, filed on Mar. 27, 2006, provisional application No. 60/276,498, filed on Mar. 19, 2001.

(51) Int. Cl.
*G06T 5/50* (2006.01)
*G02B 21/18* (2006.01)

(52) U.S. Cl. ...................... 358/474; 382/284; 382/128; 359/374

(58) Field of Classification Search ................. 358/474; 382/141, 128, 284; 359/368, 372, 373, 374
See application file for complete search history.

(56) References Cited

U.S. PATENT DOCUMENTS 6,800,249 B2 * 10/2004 de la Torre-Bueno ......... 422/63
6,943,029 B2    9/2005 Copeland et al.

* cited by examiner

*Primary Examiner*—Thomas D Lee
(74) *Attorney, Agent, or Firm*—Antonio R. Durando

(57) ABSTRACT

In a scanning microscope, slides are fed automatically from a magazine to the imaging system. Each slide is labeled in some fashion with information for selecting the appropriate modality of operation of the scanner for that slide and the modality is implemented automatically. The information is preferably tied to and defined by a laboratory information system (LIS). For example, the instructions may regard the type of microscopy (i.e., trans- or epi-illumination), multi-spectral imaging with particular spectral bands combined with a particular set of z-positions, alternative filters, settings for the numerical aperture of the condenser, alternative detector operation for different resolutions, and alternative post-scan analyses of the data, as deemed optimal for the scan. The label may also contain the slide's identity, a pathologist's name, desired post-scan handling protocol, etc. The preferred array microscope to carry out the invention is also described.

12 Claims, 3 Drawing Sheets

SLIDE-BORNE IMAGING INSTRUCTIONS

RELATED APPLICATIONS

This application is based on U.S. Provisional Application No. 60/786,242, filed Mar. 27, 2006, and is a continuation-in-part application of U.S. Ser. No. 10/637,486, filed Aug. 11, 2003, which is based on PCT/US02/08286, filed Mar. 19, 2002, and claims the benefit of priority of U.S. Provisional Application No. 60/276,498, filed Mar. 19, 2001, under 35 U.S.C. Sect. 119.

BACKGROUND OF THE INVENTION

1. Field of the Invention

This invention is related in general to the field of optical microscopy. In particular, it relates to a method and apparatus for diagnostic testing of biological tissue with an array scanning microscope.

2. Description of the Related Art

Changes in the cellular structure of tissue are used to detect pathologic conditions, to assess the progress of precancerous conditions, and to detect cancer. Glass slides of tissue specimens are used for analyses of various kinds. A tissue sample is removed from a patient and is typically sectioned and fixed to a slide for staining and microscopic examination by a pathologist. The morphology of the tissue (the visually perceptible structure and shape of features in the tissue) is analyzed to provide a qualitative assessment of its condition and to identify the presence of pathologic changes, such as may indicate progression towards a malignancy. For many decades, this visual procedure has been the diagnostic mainstay of pathology.

With the advent of computers and sophisticated digital imaging equipment, researchers have extended the realm of histopathology through the use of mechanized procedures for diagnostic and quantitative investigation. Automated imaging systems are becoming more and more popular to scan the slides and record the information for computer analysis, for storage as digital files for later viewing, and for sharing via communication systems, including computer networks and the Internet. Because of the variety of tissues and analyses performed on the slides, as well as the type of scans being used, different modalities of imaging may be preferable or required for different types of samples and/or scans.

For example, in the case of brightfield whole-slide scanning, a glass slide may be imaged using red, green and blue light (RGB), or using a greater number of narrow-band channels (so-called multispectral imaging), or using several depths within the specimen (so-called z-stack imaging). RGB and multispectral imaging may be combined with z-stack imaging. Brightfield and fluorescence may also be available in the same instrument as alternative forms of imaging. Thus, as instruments become more and more capable of performing scans using such different modalities, automation will require that the instrument be also capable of selecting the best parameters of operation for each slide being scanned.

A recent innovation in the field of light microscopy utilizes a miniaturized microscope array, also referred to herein as a multiple objective array microscope, or simply as an "array microscope." As described in commonly owned International Application PCT/US02/08286, herein incorporated by reference, each miniaturized microscope includes a plurality of optical elements individually positioned with respect to a corresponding image plane and configured to image respective sections of the sample. The array microscope further includes a plurality of image sensors corresponding to respective optical elements and configured to capture image signals from respective portions of the sample.

In such an array microscope, a linear array of miniaturized microscopes is preferably provided with adjacent fields of view that span across a first dimension of the sample (also referred to herein as y direction), and the sample is translated past the fields of view across a second dimension (x direction) to image the entire sample. Because the diameter of each miniaturized microscope objective is larger than its field of view (having respective diameters of about 2 mm and 250 μm, for example), the individual microscopes of the imaging array are staggered so that their relatively smaller fields of view are offset over the second dimension (the direction of scanning) but aligned over the first dimension, as illustrated in FIG. 1. As a result of such staggered arrangement of the rows of miniaturized microscopes, the continuous strip covered by the linear scan of each optical system is substantially free of overlap with the continuous strips covered by adjacent optical systems. At each acquisition frame each miniaturized microscope projects image data for a small section of the sample object directly onto a detector and the individual frame data are then used to form an image of the entire sample object by hardware or software manipulation. Thus, the detector array provides an effectively continuous linear coverage along the first dimension which eliminates the need for mechanical translation of the microscope in that direction, providing a highly advantageous increase in imaging speed by permitting complete coverage of the sample surface with a single scanning pass along the second dimension. The details of implementation of such array microscopes are disclosed in copending U.S. Ser. No. 10/637,486.

This invention is directed at optimizing the quality of tissue images acquired with an automated imaging system that processes large numbers of slides sequentially for storage, transmission, computerized analysis, and visual inspection. Rather than manipulating the initial image obtained from a first scan to produce an improved image, or repeating a scan of the same slide under different imaging modalities after a review of the initial image, the invention is directed at using known information about the type of tissue being analyzed and the type of analysis being sought in order to optimize the imaging modalities during the first scan. The idea is to produce tissue images rapidly and sequentially that are nearly optimal for their intended use, so that their analysis (visual or computerized) can proceed directly without a need for repetitive scans.

BRIEF SUMMARY OF THE INVENTION

The invention arises out of the flexibility afforded by the array microscope described above to scan a tissue sample under a variety of different imaging modalities. Typically, many slides are fed automatically from stacks or magazines to the imaging system with an automated slide feeder, such as described in U.S. Pat. No. 6,905,300. For the purposes of the invention, each slide is labeled in some fashion (from a simple adhesive strip to a sophisticated holographic marker) with information compatible with the automated system of the scanner for selecting the appropriate modality of operation for each particular slide and the modality is implemented automatically for the scan. The information is preferably tied to and defined by a laboratory information system (LIS). Thus, each slide contains information physically affixed to it or somehow related to it in some form with specific instructions concerning the desired modality of data acquisition for that slide. For example, instructions for multi-spectral imaging with particular spectral bands combined with a particular set of z-positions, all deemed optimal for the particular tissue being scanned, may be embedded in a label affixed to the slide or the slide's magazine. A scanning instrument, for example, would automatically and reliably decode these instructions and prompt the imaging system to make the necessary adjustments to perform the imaging procedure in exact fulfillment of the order encoded on the label of the glass slide.

The imaging instructions may consist of a bar code or other two-dimensional patterns capable of being read automatically to convey information. The pattern may preferably contain additional data, such as the slide's identity and what should be done with the image data resulting from the imaging procedures (e.g., where to store, transmit, and/or display the image data). When imaging is combined with analytical technology for computerized interpretation of the data and for diagnostic tests, such as taught in U.S. Ser. 10/602,756, the encoded information may also contain instructions regarding optimal such post-scan analysis. Thus, as the functionality of the imaging instrument is broadened by technological improvements, the imaging-procedure instructions may also include instructions regarding the application of image-analysis algorithms to the image data collected by the scan.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

Figure 1:
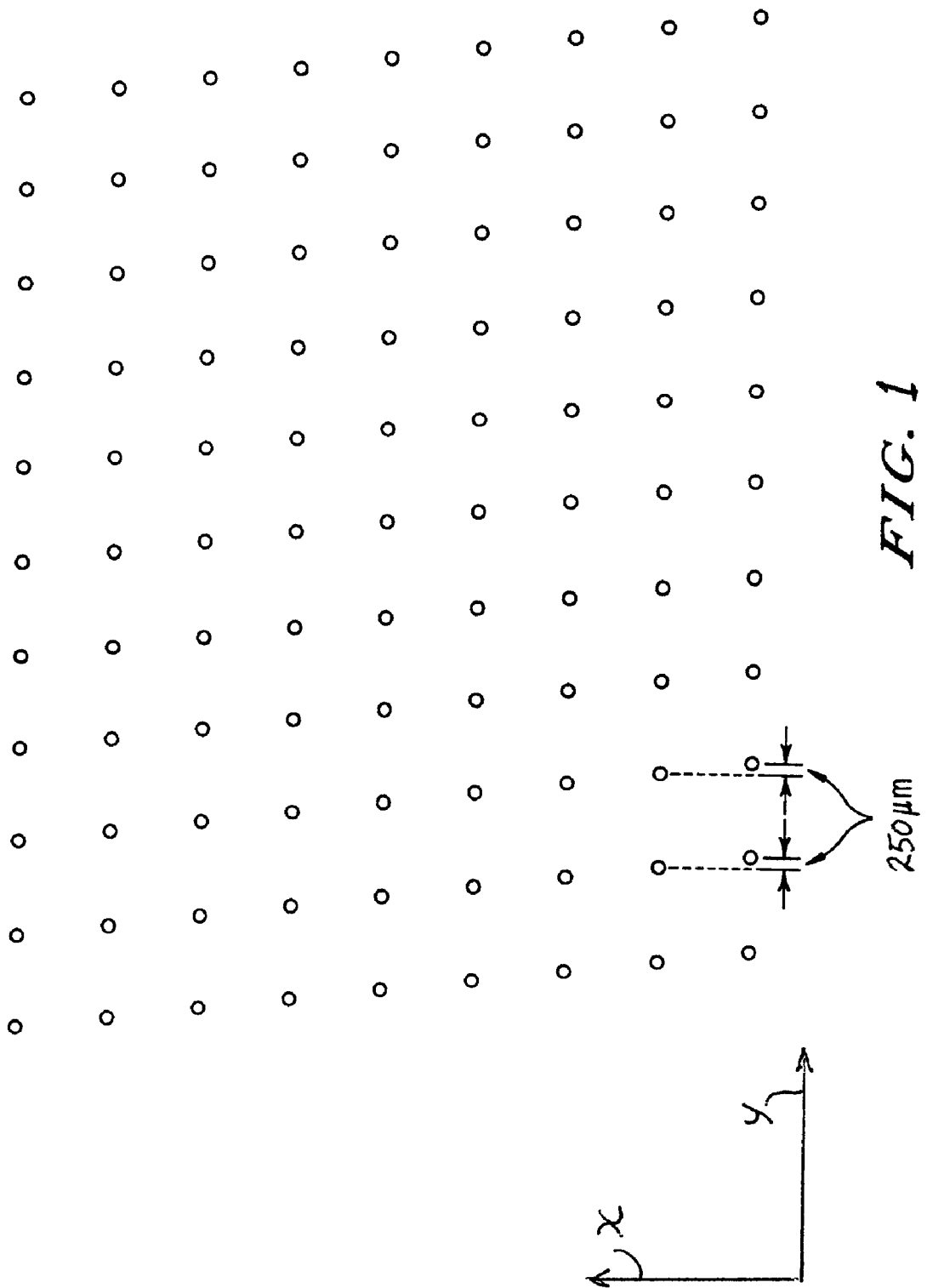
FIG. 1 is a simplified schematic representation of the fields of view in an array-microscopes layout of 99 miniaturized microscopes in an array of 9 rows of individual microscopes disposed transversely and 11 columns of microscopes disposed at a slight angle, respectively, with respect to the direction of scanning, such that a complete coverage of the sample surface is achieved during a scan.

DESCRIPTION OF THE PREFERRED
EMBODIMENTS OF THE INVENTION

The invention is based on the realization that technical advances made in the field of optical microscopy afford an opportunity for greatly improved histopathology. In particular, the advent of the array microscope described in Ser. No. 10/637,486, together with the many improvements to that microscope disclosed in U.S. Pat. Nos. 6,842,290, 6,905,300, 6,950,241, 6,958,464, 6,987,259, 7,019,895, 7,023,622, 7,034,317, 7,061,584, 7,113,651, and 7,116,437, in U.S. Published Applications No. 2004/0223632, No. 2004/0264757, No. 2005/0084175 and No. 2005/0088735, and in Ser. No. ? (to be provided by amendment upon receipt from PTO—"Liquid Lens . . . "), all hereby incorporated by reference, affords an untapped resource for optimizing the exploitation of the information carried in each slide. The degree of flexibility provided by these improvements with regard to extracting the largest possible amount of information from each sample is unparalleled in the history of histopathology. This invention enables the automatic implementation of such a strategy.

As used herein, the terms "mode" and "modality" of operation, with regard to the process of acquiring image data during the optical scan of a sample, are intended to refer to any parameter setting or other variable that may be implemented by the optical system at hand. Such parameters may include, without limitation, colors or combinations of colors used by the lighting system during the scan (including different relative levels of color illumination, and different fluorescence excitation wavelengths, or emission filters); types of illumination used (i.e., trans-illumination, epi-illumination, fluorescence, or two-photon microscopy); different focal planes at which imaging may be carried out (i.e., different z-elevations of the microscope array or different focal planes of individual microscopes in the array with respect to the sample); different numerical apertures of individual microscopes in the array ; different detector strategies (such as the use of alternative sets of detector pixels, or repeated scans with a shift in the detector alignment) for different image resolutions; alternative post-scan analysis techniques; post-scan data handling instructions (display and/or print and/or store and /or transmit); changes to the illumination system to effect imaging with a preset degree of partial coherence, such as reducing the diameter of the aperture diaphragm (including using multiple wavefront deformation functions applied substantially at the microscope aperture stop or its conjugate image plane to correct spherical aberration; adjustment of the tissue-detection algorithm parameters to compensate for different tissue types or different levels of stain in the mounting medium and therefore achieve more accurate detection of tissue on each slide (such as using multiple threshold values in tissue detection); adjustment of the wavefront deformation in each objective in the array microscope for a coverslip or tape thickness value that deviates from the value of that thickness as used in the design of the objective (e.g., 170 microns) to compensate for spherical aberration introduced by the actual thickness of the coverslip or tape; and activation of a phase element in the pupil of each objective in the array microscope to enable extended depth-of-field imaging.

With reference to the array microscope described herein as the preferred optical system to carry out the invention, the term "microscope" is used not only in its generic sense but also with reference to both the array microscope and the individual miniaturized microscopes within the array described in International Application PCT/US02/08286, and it is assumed that the distinction will be apparent to those skilled in the art from the context of the description. With reference to the scanning direction of the imaging system of the invention, as claimed, the term "linear" is intended to cover a straight as well as a curvilinear path during which each objective of the microscope array acquires image data (light intensity) corresponding to a respective straight or curvilinear continuous strip of the object. Finally, with reference to the image data acquired by the scanning microscope of the invention, the term "processing" is intended to include any kind of data manipulation, such as, without limitation, storage, transmission, analysis, calculation, mathematical conversion, and conversion to an image signal for display, printing or other form of image representation.

No current scanner has the capability of adjusting its operational configuration (apart from tissue detection and autofocus settings) for each slide based on ancillary information. According to the present invention, it is envisioned that the code on each slide will contain a full set of imaging instructions or a link to an imaging procedure programmed on the scanner. The imaging instructions can be encoded via any means, including alphanumeric characters, bar codes, 2D codes, holographic labels, phase and amplitude information. Thus, each scan can be optimized for a particular slide depending on information regarding tissue type, stains used, the computerized analysis intended for the sample, the visual analysis normally conducted or requested by pathologists with this type of tissue, etc. The following examples illustrate the invention.

Sections of bone tissue are known to exhibit rapidly changing topography (i.e., the height of the sample surface varies greatly with respect to the depth of focus of the microscope). Consequently, a slide bearing such a specimen should automatically trigger a z-stack imaging sequence. That is, the slide should be imaged repeatedly at different focal planes before moving on to the next slide.

A section derived from a breast biopsy frequently contains fat cells (essentially empty regions surrounded by "wispy" looking lattice). Under normal imaging conditions suitable for capturing tissue structure without such sparse areas, the image of a fat cell may not show sufficient contrast to be detected during a pre-can. Therefore, a slide containing such tissue (which would normally be detected during the pre-scan conventionally performed to acquire data used to optimize focus during the subsequent imaging scan) could trigger an adjustment to the tissue detection method so as not to leave out any part of the tissue section being imaged. For example, the sensitivity and the specificity of the tissue detection method could be changed to increase its sensitivity to faint regions on the slide. In simple terms, the detection threshold for separating tissue signals from background signals would be lowered from the nominal value used for tissue sections of more uniform optical density.

If the scanner is capable of reading a tissue stainer recipe bar-code (e.g., as used by Ventana Medical Systems, described in U.S. Pat. No. 6,943,029) or another type of graphic representation of the same information, the illumination colors may be adjusted in order to create maximum contrast by choosing wavelengths that correspond to an optimal part of the stain's absorption spectrum. For example, when imaging a tissue section stained with hemotoxylin and eosin, one of the illumination colors should be chosen to be near or at the absorption peak of eosin (525 nm). However, when imaging a tissue section stained with hemotoxylin and the brownish diaminobenzidine (DAB), contrast is enhanced by using illumination colors with wavelengths in the ranges of 385-430 nm, 480-500 nm, and 575-585 nm Given the particular pathologist to whom the case is assigned, the aperture diaphragm of the condenser in the microscope may be closed or opened by the scanner to suit the preferences of that pathologist regarding partial coherence of the slide illumination. As those skilled in the art understand, reducing the numerical aperture of the condenser produces the apparent effect of sharpening the image and increasing contrast, an effect considered desirable by some viewers. Furthermore, the spectral content of the illumination in the scanner may be adjusted by changing the relative light levels of illumination colors to fit the preference of the pathologist for the color representation in the viewed image. For instance, images may be acquired at spectral-illumination-source (such as LED) electrical-current settings adjusted to the preference of the pathologist for the color representation in the viewed image. Therefore, the imaging preference of the pathologist may also be embedded within each slide's set of instructions.

If the tissue being scanned has been stained with one or more fluorescent contrast agents (e.g., Alexa Fluor 488 or quantum dots), then the code on the slide may instruct the scanner to activate one or more excitation wavelengths, or one or more emission filters (or equivalent means of capturing spectral data), and whether or not a brightfield image should be captured along with the fluorescent image or images.

In the case of histological slides, the scanner may be instructed to scan at a lower resolution (e.g., a sampling distance of 470 nm/pixel). In the case of cytological preparations, the scanner may be instructed to scan at a higher resolution (e.g., a sampling distance of 235 nm/pixel or less) and at multiple depths within the slide.

In addition, if instructions from a laboratory information system (LIS) to the scanner include the number of slides and the type of stain on each slide, the scanner could also be programmed to perform the following functions (without limitation):

by means of colorimetric image analysis, confirm that the encoded stain information matches the actual appearance of the tissue on the corresponding glass slide;

confirm that all slides announced by the LIS/middleware have been "seen" in the scanner's queue; and verify the quality of all slides, including such effects as the presence of bubbles under the coverslip, of a delaminating coverslip, or of poor quality of tissue preparation (e.g., folds, tears, crushing of tissue).

Figure 2:
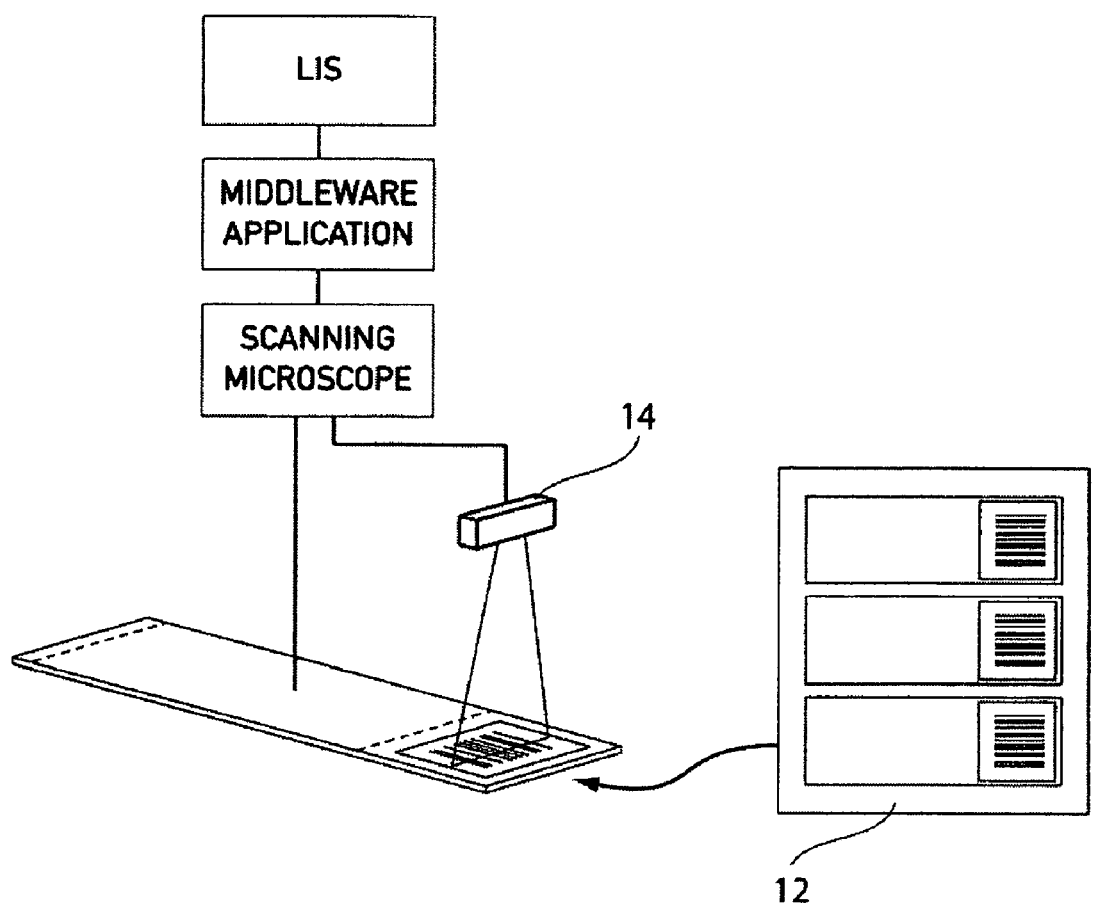
FIG. 2 is a diagram illustration of a system wherein information carried by each sample slide is used to optimize the process of image acquisition.

Note that these functions require the performance of a pre-scan dedicated to optimize the particular functions prior to the imaging scan. The scanner's "observations" of the slides during the pre-scan associated with a particular case may then be communicated back to an appropriate quality-monitoring application, such as a middleware application, or even the LIS. That is, the information gathered during the pre-scan is used to devise and implement the best modality for the scan of the slide according to some predetermined criterion programmed into the quality-monitoring application. Alternatively, the information detected from the scan of the slide is simply a source of identification (such as tissue sample, stain used, and pathologist of record) and, based on this identifying data, the best modality for the scan is obtained by direct communication with the LIS with which the slide is associated. Such a system is illustrated schematically in FIG. 2.

Figure 3:
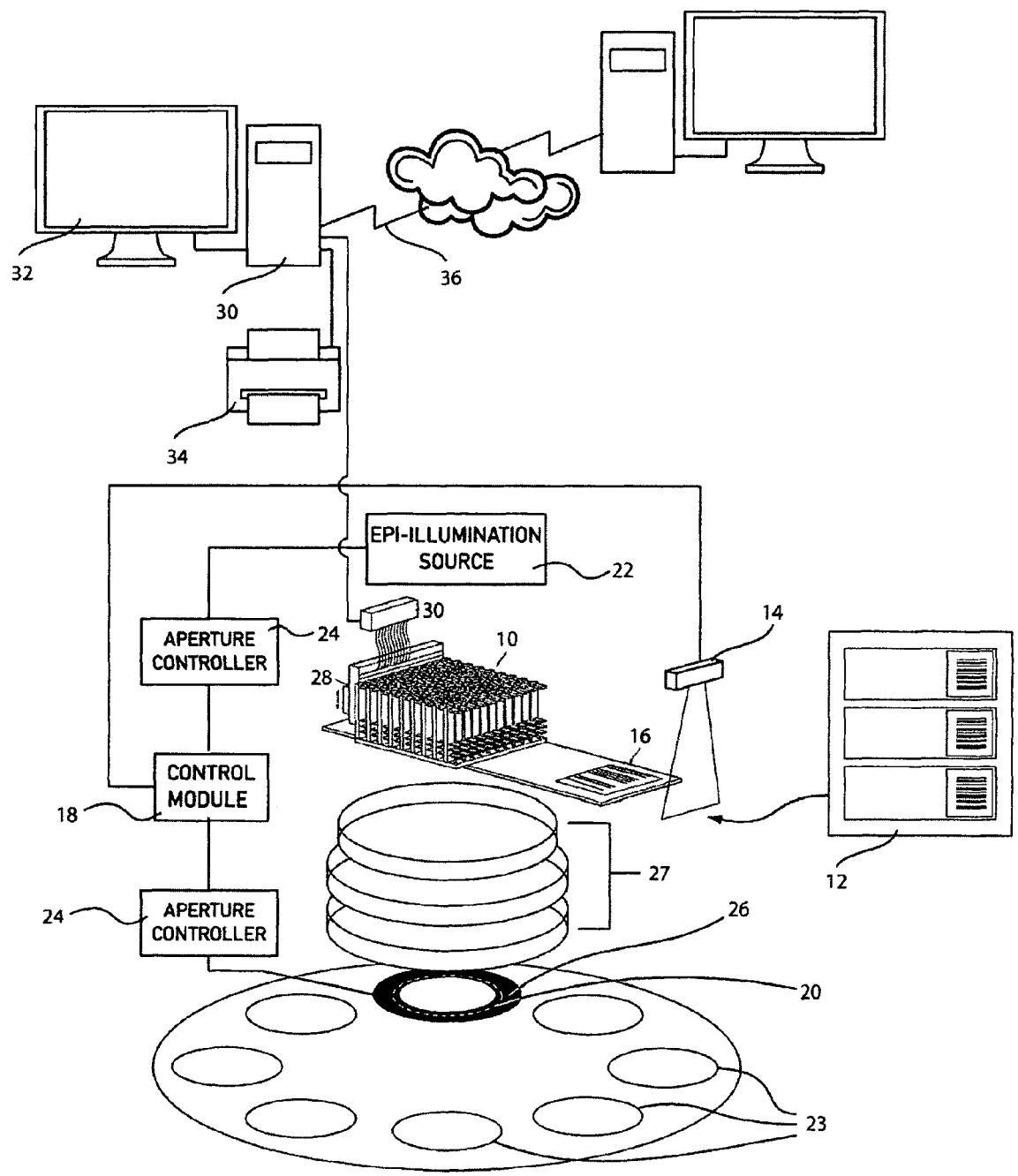
FIG. 3 shows an exemplary combination of the mechanical, optical and electronic components required to practice the invention.

FIG. 3 is an illustration of an array microscope 10, the preferred imaging system for practicing the invention, coupled to a slide feeder 12 that includes a scanner 14 for reading information incorporated with each slide 16 handled by the feeder. Based on such information, prior to scanning the slide to acquire corresponding image data, a control module 18 is utilized to translate the slide information into control signals to select the type of illumination used, such as by energizing a trans-illumination source 20 or an epi-illumination source 22. Similarly, the control module 18 may select appropriate alternative light sources 23 or filters to provide the desired illuminating wavelength. An aperture controller 24 may be used to adjust the aperture 26 of the condenser 27 to a predetermined level. A height controller 28 may be similarly instructed to adjust the focal distance of the microscope at different predetermined elevations for a sequence of scans of the same slide. The image produced by the scan may be stored in a computer 30, and/or displayed in real time on a monitor 32, and/or printed on a printer 34, and/or transmitted to another location via a telecommunications port 36. The computer 30 is used to select the predetermined combination of modalities deemed appropriate for the type of sample being processed, to coordinate all control activities of the system, and possibly to analyze the image data and coordinate other instructions for post-scan handling of the data. The computer could also be used to provide feedback to the system based on initial results from the scan, so that further adjustment could be made to optimize the end result. For example, if the wavelength selection did not provide sufficient color contrast, a different combination of sources or filters could be actuated.

Various changes in the details, steps and components that have been described may be made by those skilled in the art within the principles and scope of the invention herein illustrated and defined in the appended claims. For example, the invention has been described in the context of each slide having a label or other form of information-bearing structure associated with the slide, but the invention could be carried out also by having all information for a group of slides contained in a single instrument, such as a magazine for the group of slides, or in the first slide, or an information-transmission medium separate from the above and transmitted independently if the slides (for example, through direct communication with an LIS based on slide identifying data). Therefore, while the invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

We claim:

1. An optical scanning-microscope system comprising:
   a scanning microscope adapted to image a sample positioned on a stage;
   an automated feeder for sequentially placing multiple samples on the stage;
   a light source for illuminating the sample placed on the stage;
   a detector for capturing image data of the sample produced by the light source;
   a sensor for identifying sample information associated with each sample being fed to the stage;
   a controller for operating the system according to a set of scanning modalities prescribed by said sample information identified by the sensor; and
   a computer for processing said image data captured by the detector;
   wherein said scanning microscope comprises a two-dimensional microscope array with a plurality of magnifying imaging systems disposed along a corresponding plurality of optical axes for imaging the sample onto the detector, said plurality of magnifying imaging systems being arranged in rows and configured to image respective sections of the sample, and a scanning mechanism for producing a relative movement between the microscope array and the sample along a linear direction of scan, so as to produce an image of the sample from a plurality of image-forming signals corresponding to said plurality of magnifying imaging systems; and wherein said rows of magnifying imaging systems are staggered with respect to said linear direction of scan, such that each of the imaging systems acquires image data corresponding to a respective continuous strip of the sample along said linear direction of scan of the scanning mechanism.

2. The system of claim 1, wherein said modalities include a set of operating parameters selected from the group consisting of multiple illumination wavelengths, multiple fluorescence excitation wavelengths, multiple emission filters, trans-illumination, epi-illumination, two-photon microscopy, multiple focal planes at which imaging may be carried out, multiple numerical apertures for a condenser of the microscope, multiple image resolutions at which the detector may be operated, multiple analytical techniques for computerized post-scan analysis of the image data, multiple relative levels of color illumination, multiple wavefront deformation functions applied substantially at the microscope aperture stop or its conjugate image plane to correct spherical aberration, and multiple threshold values used in tissue detection.

3. The system of claim 1, wherein said sample information is embedded in a structure associated with said multiple samples.

4. The system of claim 1, wherein said sample information is contained in a label associated with each sample and said sensor is a scanner.

5. The system of claim 1, wherein each of said samples is a tissue section mounted on a slide.

6. The system of claim 1, wherein said modalities include a set of operating parameters selected from the group consisting of multiple illumination wavelengths, multiple fluorescence excitation wavelengths, multiple emission filters, trans-illumination, epi-illumination, two-photon microscopy, multiple focal planes at which imaging may be carried out, multiple numerical apertures for a condenser of the microscope, multiple image resolutions at which the detector may be operated, multiple analytical techniques for computerized post-scan analysis of the image data, multiple wavefront deformation functions applied substantially at the microscope aperture stop or its conjugate image plane to correct spherical aberration, and multiple threshold values used in tissue detection; each of said samples is a tissue section mounted on a slide; said sample information is contained in a label associated with each slide; and said sensor is a scanner.

7. A method of acquiring image data from a plurality of samples processed sequentially by a scanning-microscope system, the method comprising the following steps:
   automatically feeding the samples to a scanning microscope for sequentially placing each sample on a stage;
   identifying sample information associated with each sample being fed to the stage;
   adjusting the system for operation of the scanning microscope according to a set of scanning modalities prescribed by said sample information associated with each sample;
   illuminating the sample placed on the stage with a light source;
   scanning the sample placed on the stage;
   capturing image data produced by the light source with a detector; and
   processing said image data captured by the detector;
   wherein said scanning microscope comprises a two-dimensional microscope array with a plurality of magnifying imaging systems disposed along a corresponding plurality of optical axes for imaging the sample onto the detector, said plurality of magnifying imaging systems being arranged in rows and configured to image respective sections of the sample, and a scanning mechanism for producing a relative movement between the microscope array and the sample along a linear direction of scan, so as to produce an image of the sample from a plurality of image-forming signals corresponding to said plurality of magnifying imaging systems; and wherein said rows of magnifying imaging systems are staggered with respect to said linear direction of scan, such that each of the imaging systems acquires image data corresponding to a respective continuous strip of the sample along said linear direction of scan of the scanning mechanism.

8. The method of claim 7, wherein said modalities include a set of operating parameters selected from the group consisting of multiple illumination wavelengths, multiple fluorescence excitation wavelengths, multiple emission filters, trans-illumination, epi-illumination, two-photon microscopy, multiple focal planes at which imaging may be carried out, multiple numerical apertures for a condenser of the microscope, multiple image resolutions at which the detector may be operated, multiple analytical techniques for computerized post-scan analysis of the image data, multiple wavefront deformation functions applied substantially at the microscope aperture stop or its conjugate image plane to correct spherical aberration, and multiple threshold values used in tissue detection.

9. The method of claim 7, wherein said sample information is embedded in a structure associated with said multiple samples.

10. The method of claim 7, wherein said sample information is contained in a label associated with each sample and said sensor is a scanner.

11. The method of claim 7, wherein each of said samples is a tissue section mounted on a slide.

12. The method of claim 7, wherein said modalities include a set of operating parameters selected from the group consisting of multiple illumination wavelengths, multiple fluorescence excitation wavelengths, multiple emission filters, trans-illumination, epi-illumination, two-photon microscopy, multiple focal planes at which imaging may be carried out, multiple numerical apertures for a condenser of the microscope, multiple image resolutions at which the detector may be operated, multiple analytical techniques for computerized post-scan analysis of the image data, multiple wavefront deformation functions applied substantially at the microscope aperture stop or its conjugate image plane to correct spherical aberration, and multiple threshold values used in tissue detection; each of said samples is a tissue section mounted on a slide; said sample information is contained in a label associated with each slide; and said sensor is a scanner.

\* \* \* \* \*